(12) United States Patent
Heesch et al.

(10) Patent No.: US 10,478,575 B2
(45) Date of Patent: Nov. 19, 2019

(54) METHOD FOR OPERATING AN ANESTHESIA APPARATUS, ANESTHESIA APPARATUS OPERATING ACCORDING TO THE METHOD AND COMPUTER PROGRAM FOR IMPLEMENTING THE METHOD

(71) Applicant: Drägerwerk AG & Co. KGaA, Lübeck (DE)

(72) Inventors: Ralf Heesch, Lübeck (DE); Robert Schmid, Lübeck (DE); Jonas Börner, Lübeck (DE)

(73) Assignee: Draägerwerk AG & Co. KGaA, Lübeck (DE)

( * ) Notice: Subject to any disclaimer, the term of this patent is extended or adjusted under 35 U.S.C. 154(b) by 315 days.

(21) Appl. No.: 15/388,576

(22) Filed: Dec. 22, 2016

(65) Prior Publication Data

US 2017/0182271 A1  Jun. 29, 2017

(30) Foreign Application Priority Data

Dec. 23, 2015 (DE) .................. 10 2015 016 827

(51) Int. Cl.
*A61M 16/00* (2006.01)
*A61M 16/08* (2006.01)
(Continued)

(52) U.S. Cl.
CPC ........ *A61M 16/0072* (2013.01); *A61M 16/01* (2013.01); *A61M 16/024* (2017.08); *A61M 16/0883* (2014.02); *A61M 16/0891* (2014.02); *A61M 16/104* (2013.01); *A61M 16/208* (2013.01); *A61M 16/0078* (2013.01);
(Continued)

(58) Field of Classification Search
CPC .......... A61M 16/0072; A61M 16/0883; A61M 16/208; A61M 16/104; A61M 16/0891; A61M 16/024; A61M 16/01; A61M 16/0078; A61M 16/22; A61M 2016/0042;
(Continued)

(56) References Cited

U.S. PATENT DOCUMENTS

| 5,520,172 A | 5/1996 | Obermayer | |
|---|---|---|---|
| 5,575,283 A * | 11/1996 | Sjoestrand | ............ A61M 16/00 128/204.18 |
| 2002/0023646 A1 * | 2/2002 | Heesch | ................. A61M 16/01 128/204.26 |

FOREIGN PATENT DOCUMENTS

| DE | 28 22 030 A1 | 12/1978 |
|---|---|---|
| DE | 43 12 510 A1 | 10/1993 |
| DE | 100 41 007 C1 | 9/2001 |

* cited by examiner

*Primary Examiner* — Amber R Stiles
(74) *Attorney, Agent, or Firm* — McGlew and Tuttle, P.C.

(57) ABSTRACT

A method and a control program for operating an anesthesia apparatus, as well as an anesthesia apparatus (12), which operates according to the method are provided. The anesthesia apparatus includes a breathing gas feed unit (22) intended for displacing a breathing gas volume in a breathing circuit (10). A piston (23) brings about the displacement of the breathing gas. Switching over between a first mode of operation and a second mode of operation during the return of the piston (23) allows for a presetting of a corresponding piston return velocity. The piston return velocity depends on a volume flow in an exhalation branch (34) of the breathing circuit (10) in the first mode of operation. The piston return velocity depends on a minimally necessary piston return velocity in the second mode of operation.

14 Claims, 7 Drawing Sheets

(51) Int. Cl.
*A61M 16/01* (2006.01)
*A61M 16/20* (2006.01)
*A61M 16/10* (2006.01)
*A61M 16/22* (2006.01)

(52) U.S. Cl.
CPC ..... *A61M 16/22* (2013.01); *A61M 2016/0042* (2013.01); *A61M 2202/0241* (2013.01); *A61M 2205/33* (2013.01); *A61M 2205/52* (2013.01)

(58) Field of Classification Search
CPC ...... A61M 2202/0241; A61M 2205/33; A61M 2205/52
See application file for complete search history.

METHOD FOR OPERATING AN ANESTHESIA APPARATUS, ANESTHESIA APPARATUS OPERATING ACCORDING TO THE METHOD AND COMPUTER PROGRAM FOR IMPLEMENTING THE METHOD

CROSS REFERENCE TO RELATED APPLICATIONS

This application claims the benefit of priority under 35 U.S.C. § 119 of German Application 10 2015 016 827.4 filed Dec. 23, 2015, the entire contents of which are incorporated herein by reference.

FIELD OF THE INVENTION

The present invention pertains first and foremost to a method for operating an anesthesia apparatus, to an anesthesia apparatus operating according to the method and to a computer program for implementing the method.

BACKGROUND OF THE INVENTION

DE 100 41 007 C1 discloses a method for operating an anesthesia apparatus, in which a velocity, at which a piston of a piston-and-cylinder unit acting as a breathing gas feed unit is returned during an expiratory phase, is determined and preset for the most optimal recovery possible of exhaled breathing gas. Even though this method has proved to be excellent in practice, the method leads, as intended, to the above-mentioned optimal recovery of exhaled breathing gas and hence, due to the system, to a comparatively long gas change time.

SUMMARY OF THE INVENTION

Based on this, one object of the present invention is to provide a method for operating an anesthesia apparatus and an anesthesia apparatus operating according to the method with a possibility of reducing the gas change time.

According to one aspect of the invention, a method is provided for operating an anesthesia apparatus, which comprises a breathing gas feed unit intended for displacing a breathing gas volume in a breathing circuit with a piston bringing about the displacement of the breathing gas. The method automatically switches over between at least one first mode of operation and a second mode of operation during the return of the piston to preset a corresponding piston return velocity. The piston return velocity depends on a volume flow in an exhalation branch of the breathing circuit in the first mode of operation and wherein the piston return velocity depends on a minimally necessary piston return velocity in the second mode of operation.

According to another aspect of the invention an anesthesia apparatus is provided comprising a breathing circuit with a breathing gas feed unit, namely, a breathing gas feed unit in the form of a piston-and-cylinder unit. The breathing gas feed unit displaces a breathing gas volume in the breathing circuit and comprises a piston bringing about the displacement of the breathing gas during the operation. Breathing gas is displaced to the patient during an inspiratory phase and breathing gas exhaled by the patient is displaced back again into the breathing circuit during an expiratory phase. The anesthesia apparatus further comprises a control unit with associated memory. The control unit is operatively connected to the breathing gas feed unit. The control unit with associated memory is configured to execute the method according to the invention.

Provisions are made with the method according to the invention and with the anesthesia apparatus according to the invention for operating an anesthesia apparatus for the switching over being automatically possible between at least a first mode of operation and a second mode of operation during the return of the piston during an expiratory phase. With this, a particular piston return velocity is preset, for the piston return velocity being dependent on a volume flow in an expiration branch of the breathing circuit in the first mode of operation, and for the piston return velocity being dependent on a minimally necessary piston return velocity in the second mode of operation.

The advantage of the solution according to the invention is that optimal recovery of the breathing gas exhaled during the expiratory phase (first mode of operation), for example, according to the principle described in DE 100 41 007 C1, or, as an alternative, a reduction of the gas change time (second mode of operation) is possible due to the possibility of switching over between the at least two modes of operation. A combination of the two effects, i.e., an at least partial recovery of exhaled breathing gas as well as a reduction of the gas change time, is obtained in case of a combination of the two modes of operation and a switchover taking place during an expiratory phase between the first and second modes of operation.

The anesthesia apparatus may be perfected according to the features of the method described herein, such that the anesthesia apparatus comprises means for carrying out the particular embodiment of the method and of the method steps comprised thereof. Likewise, the method for operating the anesthesia apparatus may also be perfected corresponding to the functionality of the objective aspects of the anesthesia apparatus according to the invention.

In one embodiment of the method, the selection of the first or second mode of operation and a switchover between the first mode of operation and the second mode of operation depend on a setting for the fresh gas feed into the breathing circuit, which setting is performed by an operator of the anesthesia apparatus. A different selection of the first or second mode of operation and a different switchover between the first and second modes of operation, i.e., switchover at a time different from the time of switchover occurring at a low setting of the fresh gas feed and a correspondingly low fresh gas flow may possibly be obtained in case of a fresh gas feed set at a higher value and a resulting larger fresh gas flow. The desired possibility of reducing the gas change time is taken directly into account in this manner, since a larger fresh gas flow is usually selected based on a change in an anesthetic concentration (anesthetic gas concentration) introduced into the breathing circuit and a reduced gas change time is desired in case of such a change in the anesthetic concentration in order for the changed anesthetic concentration to reach the patient as quickly as possible.

In another embodiment of the method, preset limit values or limit values that can be preset by an operator concerning the setting of the fresh gas feed into the breathing circuit are taken into account for selecting the first or second mode of operation and for switching over between the first and second modes of operation. A desired fresh gas flow is preset by the operator of the anesthesia apparatus by means of a setting for a fresh gas feed into the breathing circuit. For example, a low fresh gas flow and a high fresh gas flow are defined by means of the preset or presettable limit values.

For example, a switchover into the first mode of operation will automatically take place if the fresh gas flow set by the operator is lower than the low fresh gas flow defined by the respective limit value. If the set fresh gas flow is greater than the high fresh gas flow defined by the respective limit value, a switchover into the second mode of operation will automatically take place. If the set fresh gas flow is between a low fresh gas flow and a high fresh gas flow, a switchover will automatically take place between the first mode of operation and the second mode of operation during a phase of exhalation.

In a special embodiment of a method in which such limit values are taken into account, the switchover between the first mode of operation and the second mode of operation takes place automatically at a fresh gas flow set by the operator between a low fresh gas flow and a high fresh gas flow corresponding to an interpolation related to the two limit values. The closer the fresh gas flow set by the operator is in the range of the lower value, the more will the resulting piston return velocity correspond to the first mode of operation, and the closer the set fresh gas flow is in the range of the upper limit value, the more strongly will the resulting piston return velocity correspond to the second mode of operation. The later the time at which the switchover takes place between the first and second modes of operation is, the respective resulting piston return velocity will correspond all the more to the piston return velocity according to the first mode of operation, and the earlier the time at which the switchover between the first and second modes of operation takes place is, the respective resulting piston return velocity will all the more correspond to the piston return velocity according to the second mode of operation.

In yet another embodiment of the method, the limit values are determined automatically by the anesthesia apparatus, namely, by means of a control unit of the anesthesia apparatus, based on at least one demographic variable of the patient. The operating method is optimally adapted in this manner to the particular patient. Demographic variables of the patient are, for example, age, gender, height, and body weight.

In addition or as an alternative to a possibility of adapting a gas change time by influencing a piston return velocity, the gas change time can also be adapted by a method for operating an anesthesia apparatus, in which a zero position of the piston of the breathing gas feed unit is changed automatically incrementally as a function of a volume reserve and a particular, applied inspiratory tidal volume. If an examination of the volume reserve and the particular tidal volume applied shows a volume excess, the zero position of the piston can be changed incrementally, so that a reduction of the volume excess will result. Such a reduction of the volume excess leads to a reduction of the quantity of gas being moved by means of the breathing gas feed unit and hence to a reduced gas change time.

The zero position of the piston and a changed volume reserve resulting from a change in the zero position of the piston are changed asymmetrically in a special embodiment of this variant of the method. The asymmetric change takes place such that a possible reduction of the volume reserve from one ventilation cycle to a next ventilation cycle is smaller than a possible increase in the volume reserve. It is guaranteed in this manner that a substantial reduction of the volume reserve takes place only in the form of a plurality of "small" increments for changing the zero position of the piston and correspondingly only in case of a volume excess that is stable over the long term, whereas the system responds with a "great" increment compared to this in case of a volume deficit and sets an increased volume reserve.

If the change in the zero position of the piston is limited in one embodiment of the method by at least one preset limit value or a limit value presettable by the operator concerning a resulting changed volume reserve, an operator of the anesthesia apparatus can influence the incremental change in the zero position by presetting or changing such a limit value. Provisions are preferably made in this connection for such a limit value to be determined automatically by the anesthesia apparatus, namely, a control unit of the anesthesia apparatus, based on a demographic variable of the patient, for example, the body weight or the age of the particular patient.

The above-mentioned object is also accomplished by an anesthesia apparatus that operates according to the method as here and hereinafter described and comprises therefor means for carrying out the method. The method of the present invention is preferably implemented in software. Thus, another aspect of the present invention is a computer program acting as a control program with program code instructions executable by a computer, on the one hand, and, on the other hand, a storage medium with such a computer program, i.e., a computer program product with program code, and, finally, also a control device, in the memory of which such a computer program is or can be charged as a means for carrying out the method and the embodiments thereof.

The computer program is intended for being executed by the control device of the anesthesia apparatus. When method steps or sequences of method steps are described below, this pertains to actions that take place based on the computer program or under the control of the computer program, unless it is expressly stated otherwise that individual actions are prompted by an operator of the anesthesia apparatus. Any use of the term automatic and automatically means at least that the action in question takes place on the basis of the computer program or under the control of the computer program or control unit configured to execute the method.

Instead of executing the method by means of a control program with individual program code instructions, the method being here and hereinafter described may also be implemented in the form of firmware. It is clear to the person skilled in the art that implementation in firmware or in firmware and software or in firmware and hardware is also always possible instead of an implementation of a method in software. It shall therefore apply to the description being presented here that the term software or the terms control program and computer program also comprise other possibilities of implementation, namely, especially an implementation in firmware or in firmware and software or in firmware and hardware.

An exemplary embodiment of the present invention will be explained in more detail below on the basis of the drawings. Objects or elements corresponding to one another are provided with the same reference numbers in all figures.

The exemplary embodiment shall not be construed as a limitation of the present invention. Rather, variations and modifications are possible within the framework of the present disclosure, especially variants and combinations, which the person skilled in the art can specifically identify in connection with the features described in the general or special part of the description and are contained in the claims and/or the drawings in respect to the accomplishment of the object and lead to a new object through features that can be combined. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
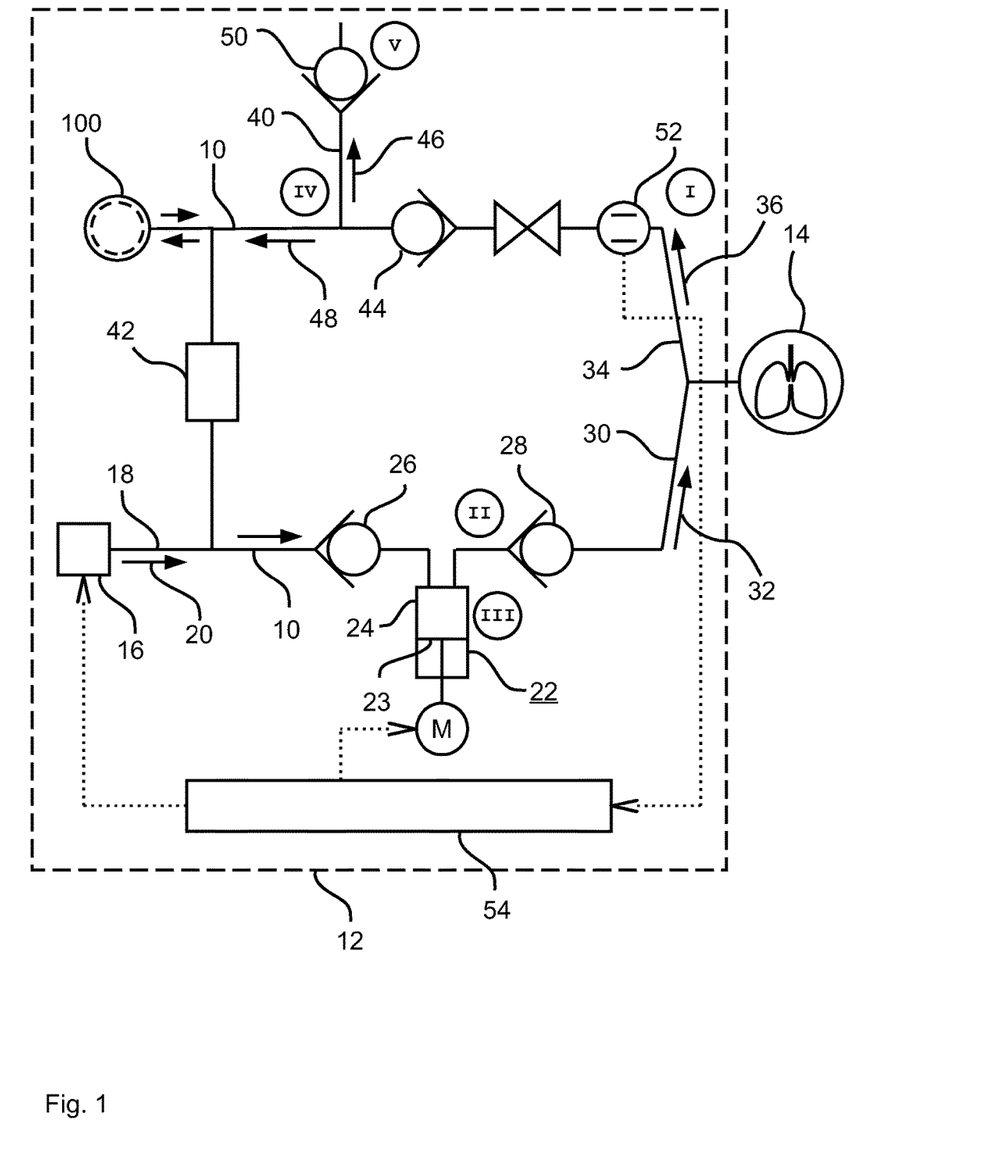
FIG. 1 is a schematic view showing an anesthesia apparatus.

Referring to the drawings, the view in FIG. 1 shows in a schematically highly simplified form a breathing circuit 10 of an anesthesia apparatus 12, which breathing circuit is reduced to the components necessary for the innovation being presented here. The ventilation of a patient 14 associated with the feed of at least one anesthetic (anesthetic gas) is carried out by means of the anesthesia apparatus 12. A breathing gas volume is moved into the lungs of the patient 14 during a phase of inhalation, and a volume of breathing gas exhaled by the patient 14 is then pushed back into the breathing circuit 10 of the anesthesia apparatus 12 during a phase of exhalation. A fresh gas containing an anesthetic is introduced into the breathing circuit 10 of the anesthesia apparatus 12 to anesthetize the patient 14 by means of a fresh gas dispensing device 16 and via a fresh gas line 18, and the breathing gas consumption of the patient 14 and possible leaks in the breathing circuit 10 are also compensated by means of the fresh gas (fresh gas flow 20) being fed.

In a manner that is known, in principle, a motor-driven breathing gas feed unit 22 is located in the breathing circuit 10 for feeding the breathing gas. The breathing gas feed unit 22 is configured in the exemplary embodiment being shown as a piston-and-cylinder unit, and the following description will be continued on this basis, but without relinquishing a continued general validity. The breathing gas feed unit 22 acts, in general, as a volume displacement device, with which at least part of the breathing gas volume present in the cylinder 24 is displaced in the direction of the patient 14 in the exemplary embodiment being shown by means of the piston 23 during a phase of inhalation. To ensure the flow direction in the breathing circuit 10, a nonreturn valve 26, 28 each is located downstream and upstream of the breathing gas feed unit 22.

Breathing gas is fed to the patient 14 via an inhalation branch during a phase of inhalation (inhalation arrow 32) and exhaled breathing gas is blown off via a breathing gas discharge line 40 from the breathing circuit 10 or circulated in the breathing circuit 10 via a $CO_2$ absorber 42 as well as by means of the breathing gas feed unit 22 during a phase of exhalation. Manual ventilation is possible by means of a manual ventilation bag 100, for example, in case of failure of a drive of the breathing gas feed unit 22 or manual intervention by the anesthesiologist is possible at any time, for example, during the induction phase prior to a surgery. The circulation of the breathing gas is maintained by means of the breathing gas feed unit 22 and maintained in the circulation direction indicated by the arrows, specifically the inhalation arrow 32 and the exhalation arrow 36, by means of the nonreturn valves 26, 28 as well as an additional nonreturn valve 44. The $CO_2$ absorber 42 brings about the purification of the breathing gas in the breathing circuit in the usual manner.

Spent breathing gas or breathing gas escaping due to possible leaks during a ventilation cycle is replaced by means of the fresh gas dispensing device 16 in the breathing circuit 10. Fresh gas is also introduced into the breathing circuit 10 when a user of the anesthesia apparatus 12, i.e., usually a corresponding medical specialist, sets a change in the concentration of the at least one anesthetic in the fresh gas, as it is common at the beginning or at the end of a surgery.

The breathing gas being exhaled by the patient is split during the exhalation into two partial flows 46, 48, namely, a first partial flow 46 indicated by a first arrow, which is removed through the breathing gas discharge line 40, and a second partial flow 48, which is shown by a second arrow and which is returned via the $CO_2$ absorber 42 into the breathing circuit 10. The splitting of the exhaled breathing gas into the two partial flows 46, 48 is due to the resistances present in the ventilation system and the setting of a breathing gas discharge valve (BGD valve) 50. The higher the prestress of the breathing gas discharge valve 50, the larger is the quantity of exhaled breathing gas and of the anesthetic gas contained therein that is returned into the breathing circuit 10.

A general goal during the operation of an anesthesia apparatus 12 is to lose the smallest possible quantity of anesthetic gas contained in the breathing gas via the breathing gas discharge line 40 at the lowest possible minimal end-expiratory pressure. The total quantity of breathing gas exhaled by the patient 14 shall ideally be returned into the breathing circuit 10 by means of the breathing gas feed unit 22.

DE 100 41 007 C1 shows a solution for this. It is proposed there that the piston 23 of the breathing gas feed unit 22 be returned during the phase of exhalation at a velocity (piston return) that is high enough for the total breathing gas volume exhaled by the patient 14 via the exhalation branch 34 to be returned again, together with new fresh gas being fed via the fresh gas line 18, into the breathing circuit 10, to be mixed with the new fresh gas (fresh gas flow 20), to be drawn into the cylinder 24 of the breathing gas feed unit 22 and to be able to be displaced to the patient 14 via the inhalation branch 30 during the next phase of inhalation.

According to the principle described in DE 100 41 007 C1, the velocity at which the piston 23 of the breathing gas feed unit 22 is returned is obtained from the sum of a volume flow measured with a volume flow sensor 52 in the exhalation branch 34 and of a volume flow being fed by means of the fresh gas dispensing device 16. The fresh gas dispensing device 16 and the motor drive of the breathing gas feed unit 22 are controlled for this by means of a control unit 54 acting as an analysis and control unit. This receives from this, as an indicator of the volume flow in the exhalation branch 34, a sensor signal from the volume flow sensor 52 located there. The resulting control of the drive of the breathing gas feed unit 22 is called flow-controlled piston return.

The principle according to DE 100 41 007 C1 can be improved upon to the extent that a change in the fresh gas concentration set by the operator of the anesthesia apparatus 12 reaches the patient 14 comparatively late, since there is a maximum return of breathing gas exhaled by the patient 14 because of the flow-controlled piston return and there is a maximum gas change time, i.e., a maximum response time of the system to a change set in the fresh gas concentration.

Provisions are made for this purpose according to the innovation according to the invention for the velocity of the piston return to be increased under certain, predetermined conditions. The resulting increase in the velocity of the piston return is an increase compared to a minimally necessary piston return velocity. This is obtained, in turn, from the volume flow (flow rate dV/dt) measured by means of the volume flow sensor 52 in the exhalation branch 34, so that the volume flow into the cylinder 24 of the breathing gas feed unit 22, which results from the piston return velocity, corresponds to the measured volume flow in the exhalation branch 34. The minimally necessary piston return velocity may accordingly also be called the minimally necessary expiratory piston return velocity. The increase in the piston return velocity causes the fresh gas being fed in a larger amount to be mixed with the breathing gas in the breathing circuit 10 and fed fresh gas and hence mixed anesthetic gas will reach the patient 14 more quickly and a reduced gas change time will correspondingly be obtained.

Figure 2:
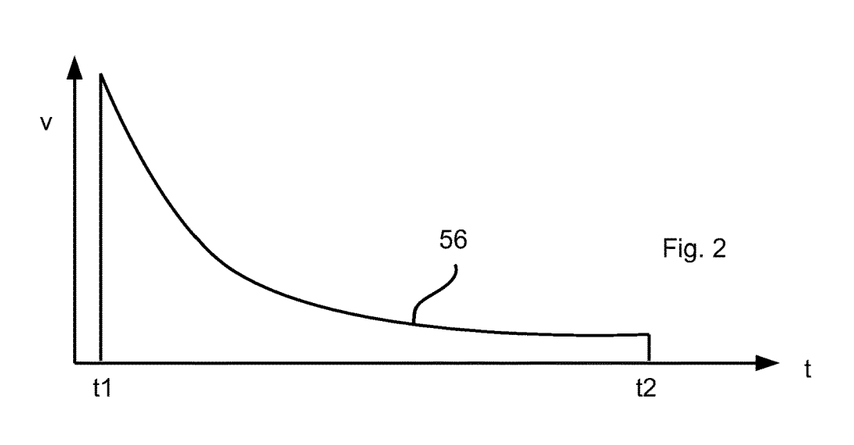
FIG. 2 is a diagram showing a velocity profile obtained during a flow-controlled piston return of a piston of a piston-and-cylinder unit of an anesthesia apparatus according to FIG. 1.
Figure 3:
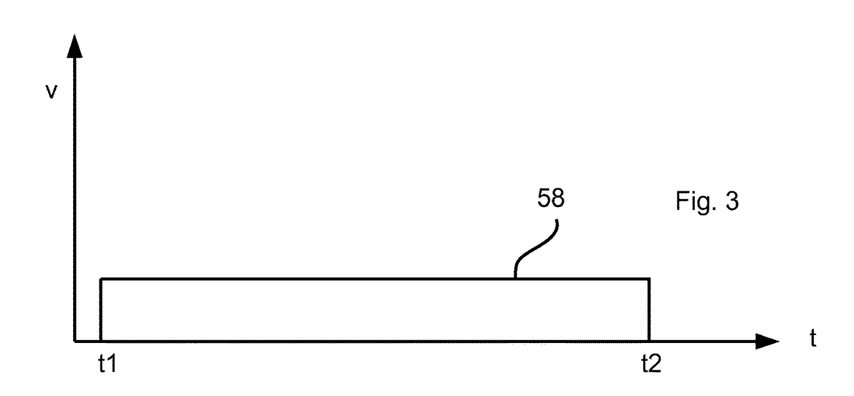
FIG. 3 is a diagram showing a velocity profile at which a shorter gas change time will result, based on the constant piston return velocity of a piston of a piston-and-cylinder unit of an anesthesia apparatus according to FIG. 1.

The diagrams in FIG. 2 and FIG. 3 show velocity profiles 56, 58 for the piston return between a first time t1 and a second time t2 during a phase of exhalation under the assumption of ideal conditions (abrupt change in velocity).

The velocity profile shown in FIG. 2 is a velocity profile as it is obtained during a flow-controlled piston return. The piston return velocity is obtained on the basis of the volume flow measured by means of the volume flow sensor 52 in the exhalation branch 34.

The velocity profile 58 shown in FIG. 3 is, by contrast, a velocity profile at which a shorter gas change time will result. Based on the constant piston return velocity, less breathing gas is drawn into the cylinder 24 of the breathing gas feed unit 22 at the beginning of the expiratory phase than is being exhaled by the patient 14. Excess breathing gas now escapes via the breathing gas discharge line 40. The constant piston return velocity corresponds to the minimally necessary piston return velocity or depends on same. If the volume flow of the breathing gas being exhaled by the patient 14 decreases and the piston return velocity continues to remain constant at the same time, this leads to an increasingly more intense mixing of the breathing gas present in the breathing circuit 10 with newly added fresh gas. The increasing uptake of fresh gas into the breathing circuit 10 leads to the shorter gas change time. However, a maximum loss of breathing gas via the breathing gas discharge line 40 will also be seen in case of a constant piston return velocity.

According to the principle according to the invention, there is a switchover between the two velocity profiles 56, 58 shown in FIG. 2 and FIG. 3 and respective underlying modes of operation as a function of a fresh gas volume flow (fresh gas flow) set by the operator of the anesthesia apparatus 12. The lower is the value at which the fresh gas flow is set, the closer shall the actual velocity profile of the piston return come to the velocity profile 56 shown in FIG. 2. On the other side, the actual velocity profile of the piston return shall come close to the velocity profile 58 shown in FIG. 3 if the fresh gas flow is set at higher values.

In return, the return of the piston 23 takes place according to a first mode of operation in case of a set minimum fresh gas flow of, for example, 1 L/min (liters per minute), and a velocity profile corresponding to the velocity profile shown in FIG. 2 is used within the framework of the first mode of operation. In case of a set maximum fresh gas flow of, for example, 8 L/min, the piston 23 returns according to a second mode of operation, and a velocity profile corresponding to the velocity profile 58 shown in FIG. 3 is used within the framework of the second mode of operation. Interpolation is performed in case of intermediate values concerning the set fresh gas flow. The interpolation is carried out as follows: At a set fresh gas flow of 4.5 L/min, this fresh gas flow is exactly in the middle between the minimum fresh gas flow (1 L/min) and the maximum fresh gas flow (8 L/min). This results in a factor of 0.5, which will hereinafter be called a weight factor. The volume flow measured by means of the volume flow sensor 52 in the exhalation branch 34 is multiplied by this factor and a necessary piston return velocity is calculated from this. As long as the piston return velocity thus calculated is greater than a minimally necessary piston return velocity obtained from a respiration rate set on the anesthesia apparatus 12 and a likewise set tidal volume, the piston 23 is returned with the calculated piston return velocity. As soon as the calculated piston return velocity drops below the minimally necessary piston return velocity, the piston 23 is returned with the minimally necessary piston return velocity. An end position is obtained for the piston return in any case from the set tidal volume. The piston return is ended when this end position is reached.

Figure 4:
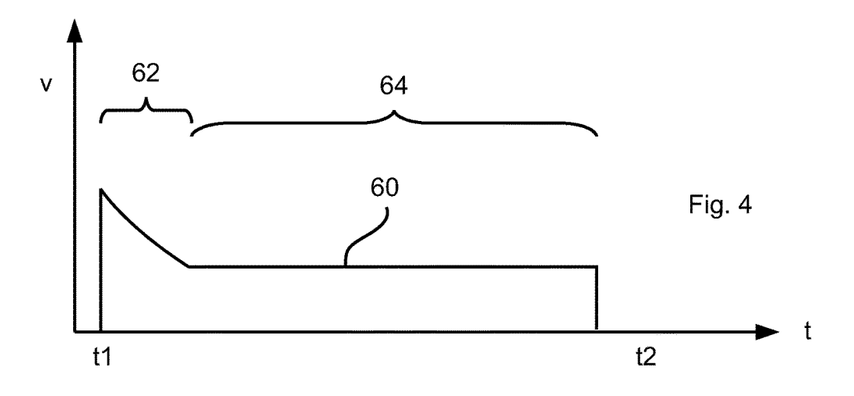
FIG. 4 is a diagram showing a piston return velocity obtained during a first section of the velocity profile as a function of the volume flow in the exhalation branch, which is weighted with a weighting factor and a piston return velocity obtained on the basis of the minimum piston return velocity during a subsequent and final, second section of the velocity profile of a piston-and-cylinder unit of an anesthesia apparatus according to FIG. 1.

The velocity profile 60 resulting on the basis of the velocity profiles 56, 58 according to FIG. 2 and FIG. 3 at a fresh gas flow of 4.5 L/min is shown in the diagram in FIG. 4. The piston return velocity is obtained during a first section 62 of the velocity profile 60 as a function of the volume flow in the exhalation branch 34, which is weighted with the weighting factor (here 0.5). The piston return velocity is obtained on the basis of the minimum piston return velocity during a subsequent and final, second section 64 of the velocity profile 60.

A general formulation of the rule for determining the piston return velocity is consequently that:

S1. a weighting factor is determined as a function of respective preset or presettable values for a maximum fresh gas flow and for a minimum fresh gas flow as well as a respective set fresh gas flow;

S2. a piston return velocity is calculated for the piston return until a preset or presettable end position is reached;

S3. the piston return velocity is calculated as a function of a volume flow in the exhalation branch 34, which is weighted with a weighting factor, S4. the calculated piston return velocity is compared to a previously determined minimum piston return velocity, S5. the piston 23 is returned at the calculated piston return velocity if this is greater than the minimum piston return velocity, and S6. the piston 23 is otherwise returned to the known end position at the minimum piston return velocity.

Figure 5:
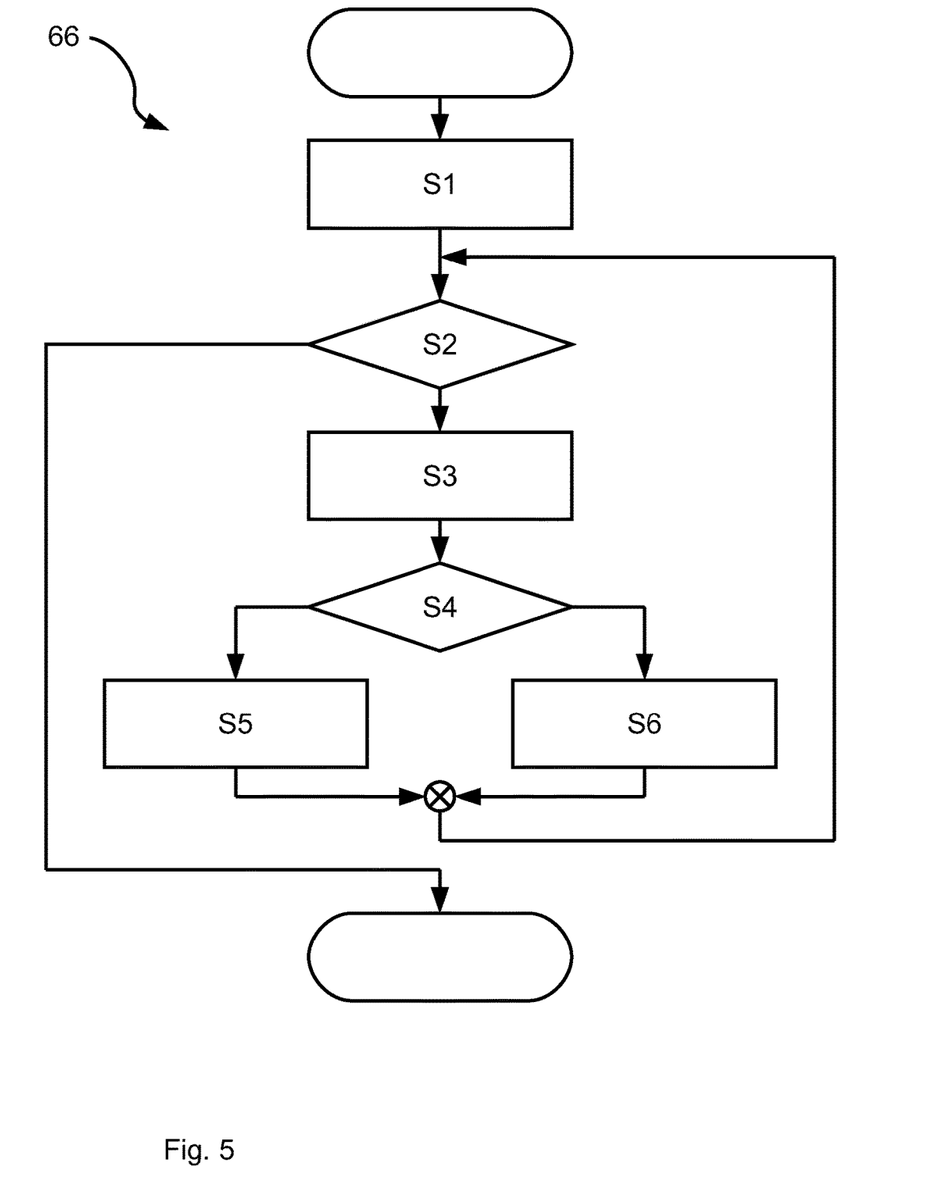
FIG. 5 is a flow chart to illustrate a method for determining a piston return velocity during an expiratory phase according to the principle according to the invention.

A graphic diagram of this determination of the piston return velocity is shown in FIG. 5 in the form of a simplified flow chart.

The numbered step S1 in the diagram in FIG. 5—is carried out before the beginning of the piston return. The numbered steps S2 through S6 are carried out cyclically during the piston return until the respective end position of the piston return is reached, and a particular cycle time is obtained from a sampling rate at which measured values of the volume flow sensor 52 are polled. Cycle times of a few msec or less are usual. The numbered steps S1 through S6 are executed under the control of the control unit 54, which has for this, in the known manner, a processing unit in the form of or in the manner of a microprocessor as well as a memory, in which a control program 66 with implementation of the numbered steps S1 through S6 are loaded, which program is executed during the operation of the anesthesia apparatus 12. The representation in FIG. 5 may thus be considered to be a form of representation of such a control program 66. The execution of the numbered step S5 corresponds to the return of the piston 23 in the first mode of operation. The execution of the numbered step S6 corresponds to the return of the piston 23 in the second mode of operation. A possible switchover between the first mode of operation and the second mode of operation takes place by means of and under the control of the control unit 54.

In a special embodiment of the innovation according to the invention, the values for the maximum fresh gas flow and for the minimum fresh gas flow are obtained automatically as a function of the age of a patient 14 (patient type) to be entered, for example, as it is indicated in the table below:

| Patient's age | Min. fresh gas flow | Max. fresh gas flow |
|---|---|---|
| Newborn | 0.5 L/min | 2.0 L/min |
| Adolescent | 1.0 L/min | 4.0 L/min |
| Adult | 1.0 L/min | 8.0 L/min |

As an alternative, different benchmark figures can be selected for the maximum and minimum fresh gas flows on the basis of other demographic variables of the patient, for example, on the basis of the particular body weight of a patient 14, of the height of the patient 14, etc. Such variables are always to be entered by the operator of the anesthesia apparatus 12, and the control unit 54 determines the particular maximum and minimum fresh gas flows for further use within the framework of the method for determining the piston return velocity. If the operator enters, for example, only the birth date of the patient 14 in question, the control unit 54 calculates the patient's age and determines the piston return velocity on the basis of the benchmark figures resulting therefrom for the maximum fresh gas flow and for the minimum fresh gas flow.

Figure 6:
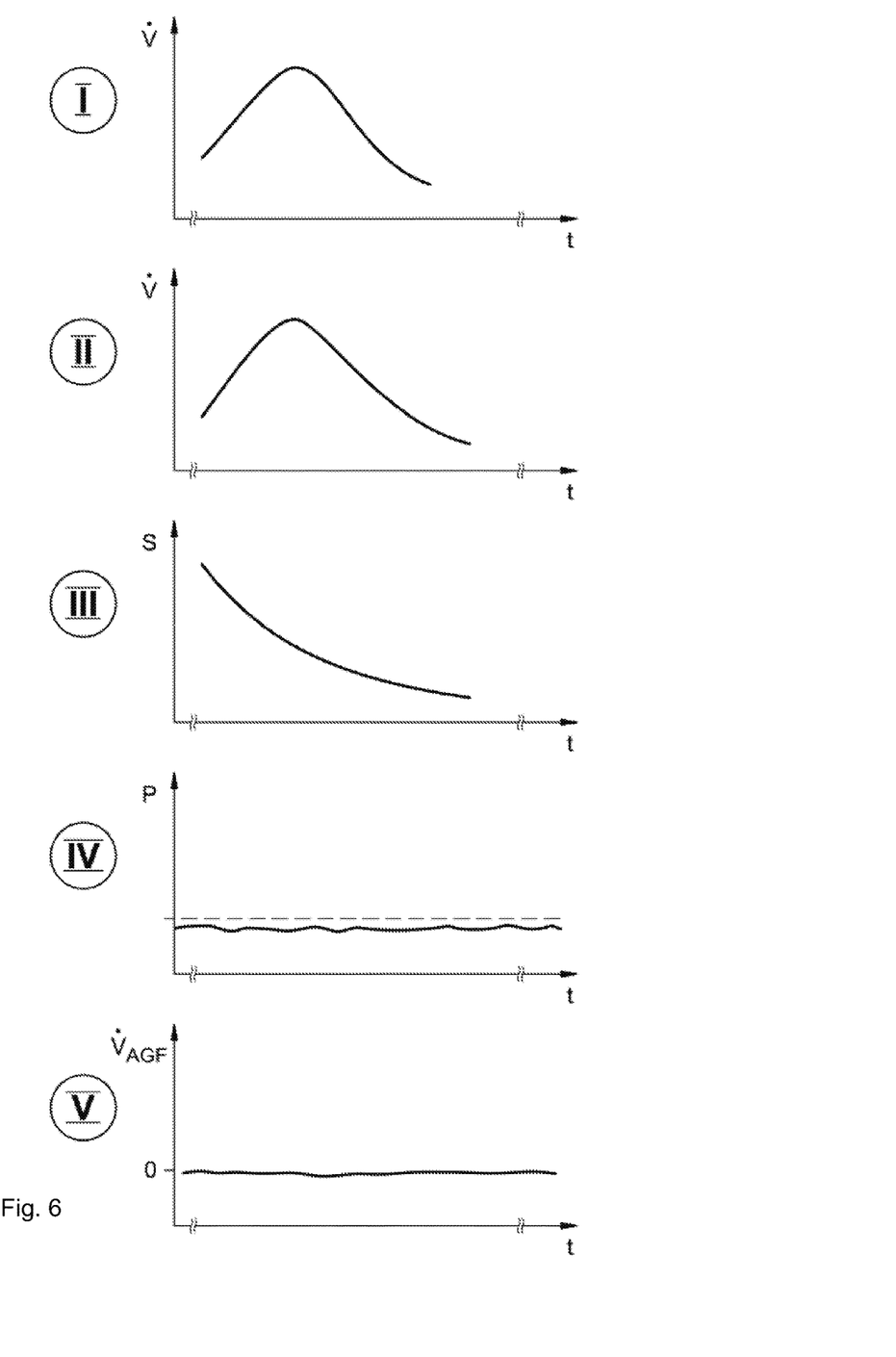
FIG. 6 is a set of graphs, in the case of the first mode of operation, of variables that are or can be recorded in a breathing circuit of an anesthesia apparatus according to FIG. 1.
Figure 7:
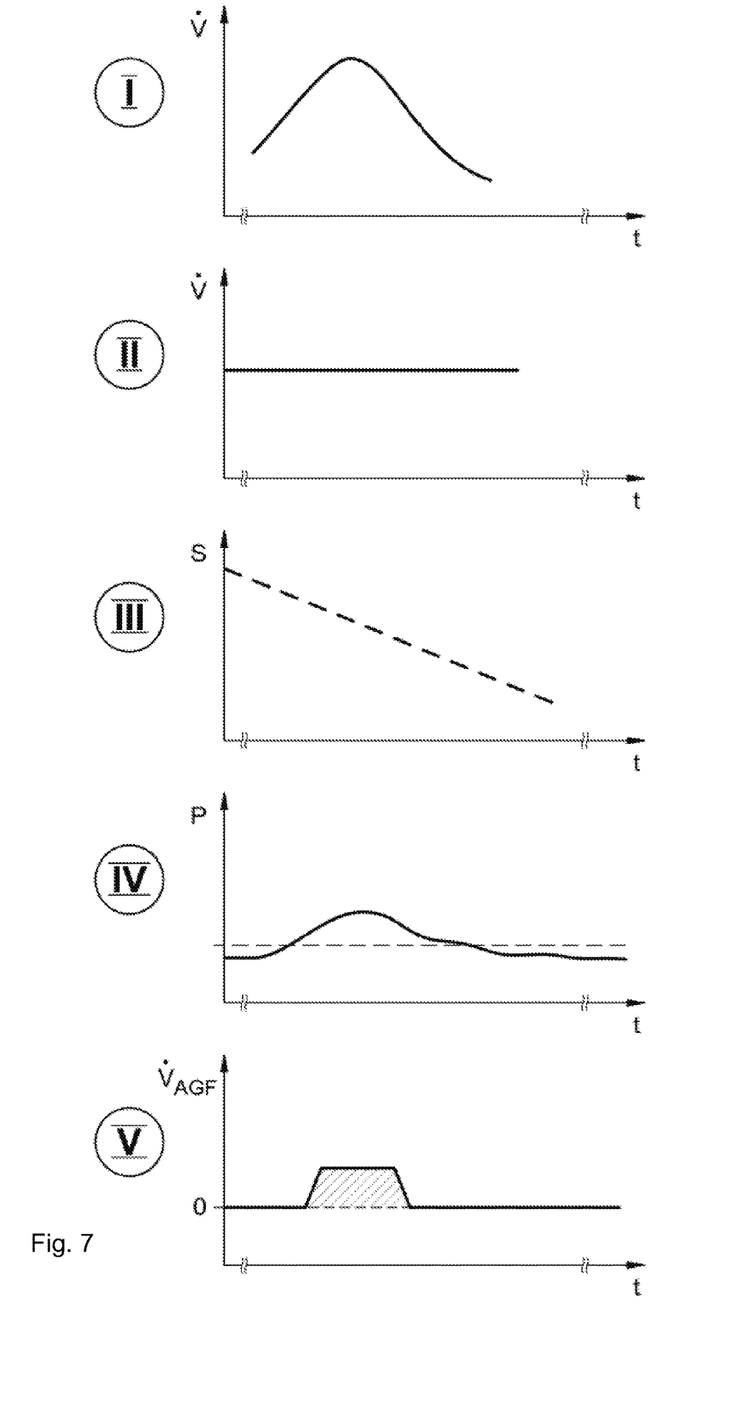
FIG. 7 is a set of graphs, in the case of the second mode of operation, of variables that are or can be recorded in a breathing circuit of an anesthesia apparatus according to FIG. 1.

The graphs in FIG. 6 and FIG. 7 show—always related to the markings I, II, III, IV and V in the view shown in FIG. 1—the conditions that become established in the different modes of operation (first mode of operation, second mode of operation) at the points designated by said markings in the breathing circuit 10.

The graphs in FIG. 6 show the situation in the case of the first mode of operation, i.e. at an initially comparatively high piston return velocity, which declines exponentially over time (cf. FIG. 2). The volume flow over time t (dV/dt) in the exhalation branch 34, as it can be detected by means of the volume flow sensor 52 (marking I) and is detected during the operation of the anesthesia apparatus 12, is shown in the top part of the graph in FIG. 6. The volume flow increases at first during the exhalation, then reaches a bell-curve-shaped maximum and finally drops. The course over time of the volume flow during the inflow into the cylinder 24 (marking II) of the breathing gas feed unit 22 with the piston 23 returned is shown under it. The maxima of the two volume flow curves at least more or less coincide. This is explained by the path/time curve during the return of the piston, which is shown in the third graph (marking III). An exponential function is obtained at least approximately as the path/time curve and the piston return velocity shown in FIG. 2 is correspondingly also at least approximately an e function. The return velocity of the piston 23 is obtained corresponding to the quantity of the breathing gas volume displaced into the breathing circuit 10 during the exhalation. In other words, the piston 23 is returned at such a velocity that the breathing gas volume displaced back into the breathing circuit 10 is taken up fully by the cylinder 24. The piston return velocity consequently depends at least on the volume flow in the exhalation branch 34 of the breathing circuit 10 (flow-controlled piston return).

The two lower graphs in FIG. 6 (markings IV and V) show the pressure/time curve at the breathing gas discharge line valve (BGD valve) 50 and the outflow of breathing gas displaced during the exhalation into the breathing circuit 10 via the breathing gas discharge valve 50. As can be seen, the pressure in front of the breathing gas discharge valve 50 (marking IV) remains below a threshold value indicated by a broken line. The pressure belonging to the threshold value is obtained on the basis of the set prestress of the breathing gas discharge valve 50. Based on the fact that the pressure in the breathing circuit 10 does not exceed the threshold value, there also is no discharge of breathing gas displaced into the breathing circuit 10 during the exhalation via the breathing gas discharge valve 50 (marking V). The breathing gas volume displaced back into the breathing circuit 10 during the exhalation consequently remains fully preserved in the breathing circuit 10 and there is no loss of breathing gas, especially no loss of anesthetic gas mixed with the breathing gas.

The graphs in FIG. 7 show the situation in the second mode of operation, i.e., with constant piston return velocity (cf. FIG. 3). The sequence of the graphs in FIG. 7 corresponds to the sequence of the graphs in FIG. 6. Consequently, the volume flow over time t (dV/dt) in the exhalation branch 34, as it can be detected by means of the volume flow sensor 52 (marking I) and is detected during the operation of the anesthesia apparatus 12, is shown at the very top. The course of the volume flow corresponds to the course explained above with reference to FIG. 6. The volume flow consequently increases at first during the exhalation to reach a bell-shaped maximum and to finally drop.

The course over time of the volume flow during the inflow into the cylinder 24 (marking I) of the breathing gas feed unit 22 with the piston 23 retracted is also shown in FIG. 7 under the course of the volume flow at the volume flow sensor 52. A marked difference can be seen here from the corresponding graph in FIG. 6 and from the first mode of operation. The volume flow is constant during the return of the piston 23. This is explained by the path/time course shown in the third graph (marking III) during the piston return. A straight line is obtained as the path/time course. The piston return velocity shown in FIG. 3 is correspondingly constant as well (the constant piston return velocity leads to a constant volume flow into the cylinder 24). The actual value of the constant piston return velocity depends here on a minimally necessary piston return velocity. The constant piston return velocity and the resulting constant volume flow into the cylinder 24 cause the breathing gas volume displaced into the breathing circuit during the exhalation not to be fully displaced into the cylinder 24 because the course of the volume flow is not linear there (FIG. 7, top graph). Instead, the threshold value set by the prestress of the breathing gas discharge valve 50 is exceeded (fourth and fifth graphs in FIG. 7) for at least a short time (fourth graph), so that the breathing gas discharge valve 50 opens and a part of the breathing gas displaced back into the breathing circuit 10 during the exhalation flows off via the breathing gas discharge valve (fifth graph). Even though the breathing gas flowing off, especially the anesthetic gas contained in the flowing-off breathing gas, is lost in this manner, fresh gas, namely, fresh gas with the newly set anesthetic concentration (anesthetic gas concentration) is drawn into the breathing circuit because the piston return velocity is constant during the entire exhalation after the maximum of the breathing gas volume being displaced back into the breathing circuit 10 and after the closure of the breathing gas discharge valve 50. This leads to a shorter gas change time.

The described principle for determining the piston return velocity makes possible a more rapid gas change. In addition or as an alternative, the zero position of the piston 23 of the breathing gas feed unit 22 can also be influenced to improve the gas change time.

Provisions are made for this for analyzing by means of the control unit 54 at the end of each inhalation, on the one hand, how large a volume was applied and, on the other hand, whether a preset or presettable volume reserve is maintained in the cylinder 24 of the breathing gas feed unit 22. A value for the volume applied during a phase of inhalation, which value can be processed numerically by means of the control unit 54, is obtained on the basis of the detection of a position of the piston 23 at the beginning and at the end of the inhalation as well as of a known cross-sectional area of the cylinder 24. As an alternative to this, such a numerically processable value can be obtained as a measured value of a volume flow sensor in the inhalation branch 30 (not shown, corresponding to the volume flow sensor 52 in the exhalation branch 34). A value for the volume reserve, which value can be processed numerically by means of the control unit 54, is obtained on the basis of the position of the piston at the end of the inhalation. The tidal volume applied during an inhalation, i.e., the tidal volume displaced to the patient 14 from the breathing gas feed unit 22, is designated by the symbol Va and the volume reserve is designated by the symbol Va. The control unit 54 analyzes the applied tidal volume Va and the currently available volume reserve Vr at the end of each inhalation. A target value for the volume reserve Vr of the next inhalation is calculated from this. To distinguish individual phases of inhalation, the current phase of inhalation is designated by the discrete time index z and the immediately preceding phase of inhalation by z−1. A difference dV/(z) between a volume reserve of the preceding inhalation Vr(z−1) and the tidal volume Va(z−1) applied during the preceding inhalation is then determined as the basis for a case differentiation:

$$dV(z)=Vr(z-1)-Va(z-1).$$

Depending on the value determined, the volume reserve is calculated for the current inhalation Vr(z) by means of the following calculation rule:

$$Vr(z)=Vr(z-1)-k1\,dV(z) \text{ if } dV(z)>0 \text{ or}$$

$$Vr(z)=Vr(z-1)+k2 \text{ if } dV(z)<0.$$

An incremental change in the volume reserve Vr and correspondingly an incremental change in the zero position of the piston 23 of the breathing gas feed unit 22 are thus obtained.

The factors k1 and k2 determine the extent of an incremental change in the volume reserve Vr. If the factors k1 and k2 are equal (k1=k2), an equal incremental change or increase in the volume reserve Vr is obtained depending on the difference determined for the case differentiation. In an advantageous embodiment, the factor k1 leading to a reduction of the volume reserve Vr is lower than the factor k2 leading to an increase in the volume reserve Vr. The consequence of this is that the volume reserve Vr is reduced appreciably in case of a long-term, stable volume excess dV(z)>0 only, whereas the volume reserve Vr is increased comparatively markedly in case of a volume deficit dV(z)<0 and the system thus responds sufficiently rapidly to changes in the tidal volume Va applied, which are due, for example, to changed settings or to a change in patient compliance. Practicable values for k1 and k2 are, for example, k1=0.1 and k2=0.5. This means that in case of a volume deficit, the volume reserve Vr is increased by half of the volume deficit determined. Compared to this, five consecutive ventilation cycles are necessary in case of a volume excess to arrive at an equal reduction of the volume reserve Vr at an equal volume excess, The implementation of the above calculation rule in a control program 66 executed by the control unit 54 to actuate the motor drive of the piston 23 with k1< >k2, especially k1<k2, is called an asymmetric interpretation of this calculation rule, since an asymmetric change is obtained in the zero position of the piston 23 and an asymmetric change in the volume reserve Vr is correspondingly obtained when the control program 66 is executed.

Figure 8:
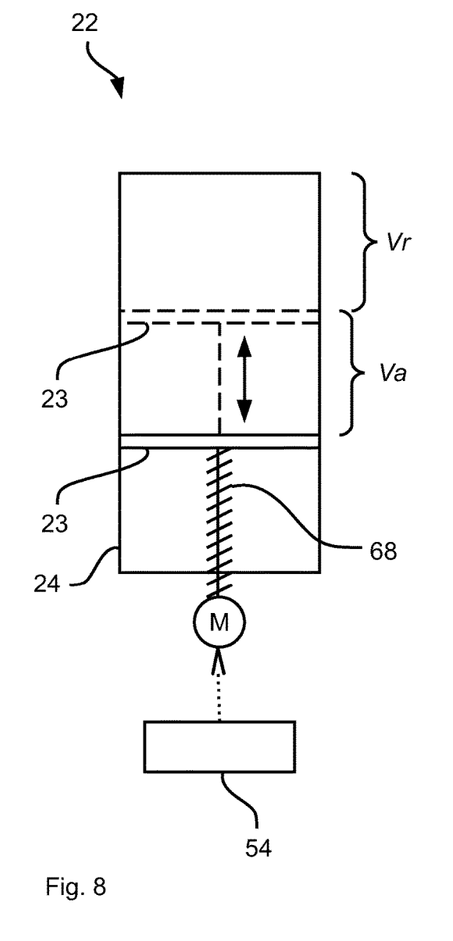
FIG. 8 is a schematic view showing a piston-and-cylinder unit of an anesthesia apparatus according to FIG. 1.
Figure 9:
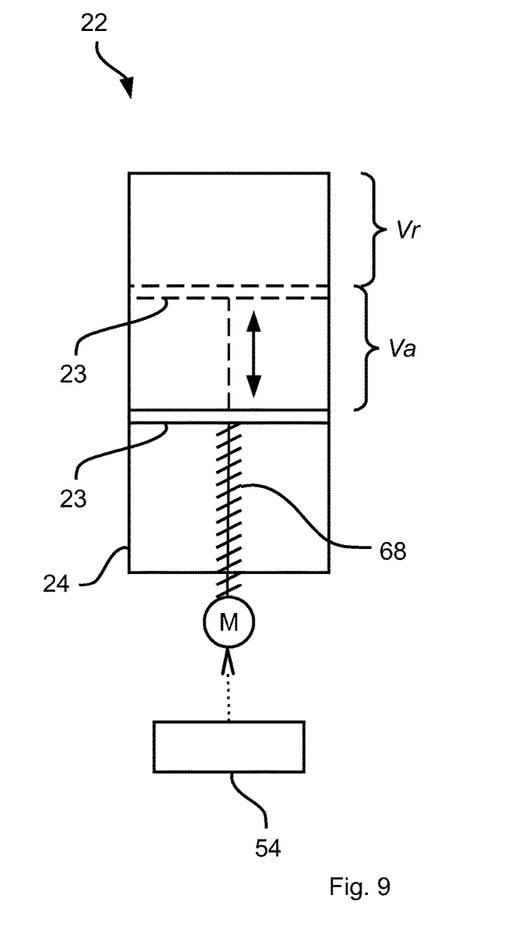
FIG. 9 is a schematic view showing the piston-and-cylinder unit of an anesthesia apparatus according to FIG. 1.

The view in FIG. 8 illustrates this on the basis of a breathing gas feed unit 22 shown in a schematically simplified manner in two exemplary operating states. The piston 23 is shown in FIG. 8 by solid lines in a position at the beginning of a phase of inhalation and by broken lines at the end of a phase of inhalation. The volume displaced from the cylinder 24 of the breathing gas feed unit 22 by means of a stroke of the piston consequently corresponds to the volume displaced to the patient 14, i.e., to the applied tidal volume Va. As is seen, a residual volume still remains in the cylinder 24 of the breathing gas feed unit 22 even when the piston 23 is in the position at the upper vertex of a piston stroke. This is the volume reserve Vr. The motor drive of the piston 23 is controlled by means of the control unit 54, on the one hand, for cyclically generating a piston stroke during a phase of inhalation and a subsequent phase of exhalation, and, on the other hand, a zero position of the piston 23 is controlled. The piston 23 can be driven for this by means of a spindle 68, which is shown in an extremely simplified form only in the view shown in FIG. 8. The view in FIG. 9 shows the result of an incremental change in the zero position of the piston 23 according to the principle according to the invention and the resulting change—here a reduction—in the volume reserve Vr. A lower or upper vertex of the cyclical motion of the piston during a phase of inhalation and subsequent phase of expiration may equally be considered to be a zero position of the piston 23. A reduction of the volume reserve Vr leads to a more rapid gas change time because of the reduction in the volume reserve Vr, which is associated herewith. Reference shall be made to DE 43 12 510 A1 (corresponding to U.S. Pat. No. 5,520,172 which is hereby incorporated by reference in its entirety) and DE 28 22 030 A1, whose full disclosure contents shall thus be considered to be included in this application, for further details in respect to a spindle drive of the piston 23.

Figure 10:
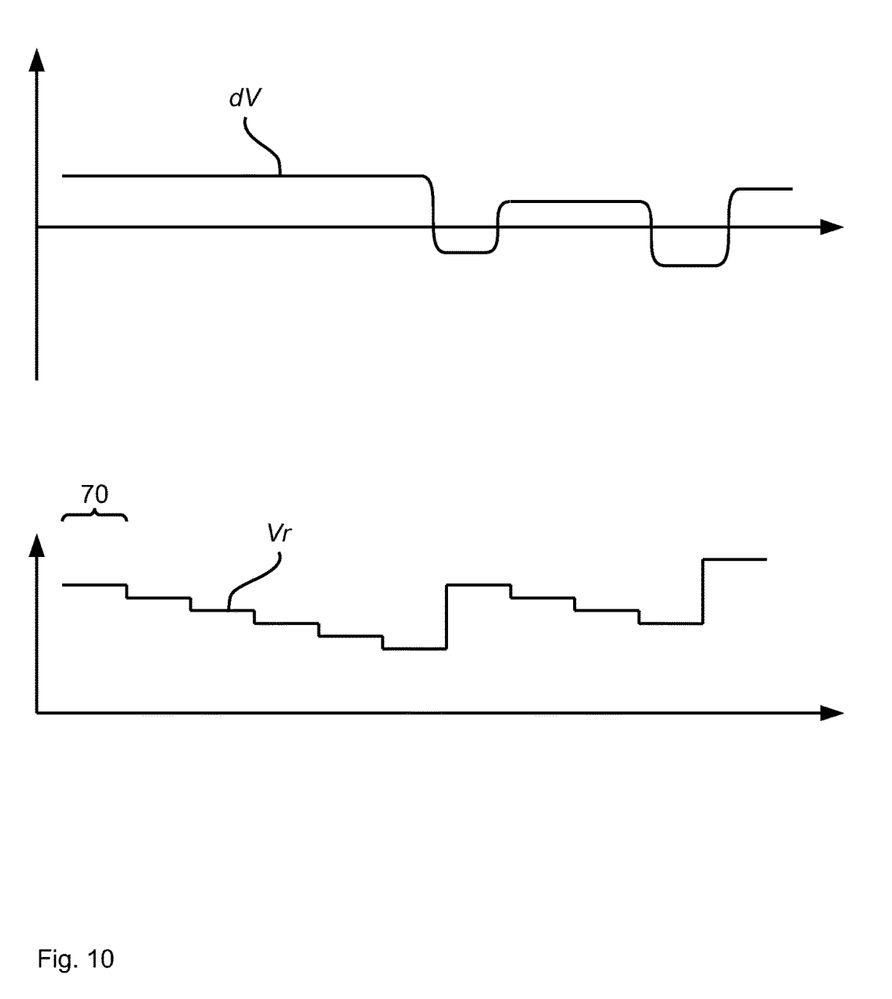
FIG. 10 is a set of graphs showing an incremental change in a volume reserve as a measure for adapting a gas change time.

The view in FIG. 10 shows an incremental change in the volume reserve Vr resulting from the application of the above calculation rule as a function of a volume excess dV(z)>0 or volume deficit dV(z)<0 at the end of the phase of inhalation of the respective ventilation cycle 70.

The change in the zero position of the piston 23 and the resulting changed volume reserve Vr are limited by at least one preset or presettable limit value. The consequence of the use of such a limit value is that the volume reserve Vr cannot drop below the corresponding limit value even when the calculation rule is applied. Such a limit value can be entered by the operator. In addition or as an alternative, provisions may be made for the limit value to depend on a demographic variable of the patient, for example, the age, gender, etc., of the patient 14 and to be determined automatically during the operation of the anesthesia apparatus 12 by means of the control program 66 on the basis of such a demographic variable of the patient. Practicable lower limit values for the volume reserve Vr are, for example, 200 mL for newborns, 450 mL for adolescent patients 14 and 600 mL for adult patients 14. An entered age or date of birth of the patient 14 is taken into account when implementing an automatic limit value determination as a partial function of the control program 66 and the corresponding limit value is selected on the basis of a table. One or more upper limit values may also be taken into account in the same way, as one or more lower limit values may also be taken into account when the calculation rule is applied, so that the volume reserve Vr will not exceed a value defined by the respective limit value. In addition, at least one lower limit value and at least one upper limit value are taken into account when the calculation rule is applied, so that it is ensured that the physically possible adjustability of the piston position is taken into account.

Individual essential aspects of the description being presented here can finally be briefly summarized as follows. A method for operating an anesthesia apparatus 12, an implementation of the method in the form of a control program 66 as well as an anesthesia apparatus 12 operating according to the method are described. The anesthesia apparatus 12 comprises a breathing gas feed unit 22, which is intended for displacing a breathing gas volume in a breathing circuit 10 by means of a piston 23. It is possible to switch automatically over between at least a first mode of operation and a second mode of operation in the method during the return of the piston 23 during a phase of exhalation for presetting a corresponding piston return velocity, the piston return velocity depending in the first mode of operation on a volume flow in an exhalation branch 34 of the breathing circuit 10 and the piston return velocity depending on the second mode of operation on a minimally necessary piston return velocity in the second mode of operation.

While specific embodiments of the invention have been shown and described in detail to illustrate the application of the principles of the invention, it will be understood that the invention may be embodied otherwise without departing from such principles.

What is claimed is:

1. A method for operating an anesthesia apparatus comprising a breathing gas feed unit for displacing a breathing gas volume in a breathing circuit, wherein the breathing gas feed unit comprises a piston bringing about the displacement of the breathing gas, the method comprising the steps of:
automatically switching over between at least one first mode of operation and a second mode of operation during a return of the piston to preset a corresponding piston return velocity; and
providing the piston return velocity to depend on a volume flow in an exhalation branch of the breathing circuit in the first mode of operation; and
providing the piston return velocity to depend on a minimally necessary piston return velocity in the second mode of operation;
wherein the selection of the first or second mode of operation and the switchover between the first and second modes of operation depends on a setting for a fresh gas feed into the breathing circuit;
wherein preset or presettable limit values are taken into account for the setting for the fresh gas feed into the breathing circuit for the selection of the first mode of operation or the second mode of operation and for the switching between the first mode of operation and the second mode of operation;
wherein a switchover takes place between the first mode of operation and the second mode of operation based on an interpolation related to the limit values.

2. A method in accordance with claim 1, wherein the limit values are determined automatically on the basis of a demographic variable of the patient.

3. A method in accordance with claim 1, wherein a zero position of the piston of the breathing gas feed unit is changed incrementally as a function of a volume reserve and an applied inspiratory tidal volume.

4. A method in accordance with claim 3, wherein the zero position of the piston and a changed volume reserve resulting from a change in the zero position of the piston are changed asymmetrically, such that a possible reduction of the volume reserve is smaller from one ventilation cycle to a next ventilation cycle than a possible increase in the volume reserve.

5. A method in accordance with claim 3, wherein the change in the zero position of the piston is limited by at least one preset or presettable limit value for a resulting, changed volume reserve.

6. A method in accordance with claim 5, wherein:
preset or presettable limit values are taken into account for the setting for the fresh gas feed into the breathing circuit for the selection of the first mode of operation or the second mode of operation and for the switching between the first mode of operation and the second mode of operation; and
the limit value is determined automatically based on a demographic variable of the patient.

7. A method according to claim 1, further comprising:
providing a computer program with program code to execute the steps of automatically switching, providing the piston return velocity to depend on a volume flow in an exhalation branch of the breathing circuit in the first mode of operation and providing the piston return velocity to depend on a minimally necessary piston return velocity in the second mode of operation; and executing the computer program with a control unit of the anesthesia apparatus.

8. An anesthesia apparatus comprising:

a breathing circuit;

a breathing gas feed unit for displacing a breathing gas volume in the breathing circuit, the breathing gas feed unit comprising a piston bringing about the displacement of the breathing gas; and a control unit with associated memory, the control unit being operatively connected to the breathing gas feed unit, the control unit with associated memory being configured to:

automatically switch over between at least one breathing gas feed unit first mode of operation and a breathing gas feed unit second mode of operation during a return of the piston to preset a corresponding piston return velocity; and provide the piston return velocity to depend on a volume flow in an exhalation branch of the breathing circuit in the first mode of operation; and provide the piston return velocity to depend on a minimally necessary piston return velocity in the second mode of operation;

a fresh gas dispensing device operatively connected to the breathing gas feed unit and operatively connected to the control unit, wherein the control unit with associated memory selects the breathing gas feed unit first mode of operation or the breathing gas feed unit second mode of operation and switches over between the breathing gas feed unit first mode of operation or the breathing gas feed unit second mode of operation depending upon a setting of the fresh gas dispensing device for a fresh gas feed into the breathing circuit;

wherein the control unit with associated memory has preset or receives limit values and sets the fresh gas feed into the breathing circuit as a function of the limit values for the selection of the first mode of operation or the second mode of operation and for the switching between the first mode of operation and the second mode of operation;

wherein a switchover takes place between the first mode of operation and the second mode of operation based on an interpolation related to the limit values.

9. An anesthesia apparatus in accordance with claim 8, wherein the limit values are determined automatically on the basis of a characteristic variable of the patient.

10. An anesthesia apparatus in accordance with claim 8, wherein a zero position of the piston of the breathing gas feed unit is changed incrementally as a function of a volume reserve and an applied inspiratory tidal volume.

11. An anesthesia apparatus in accordance with claim 10, wherein the zero position of the piston and a changed volume reserve resulting from a change in the zero position of the piston are changed asymmetrically, such that a possible reduction of the volume reserve is smaller from one ventilation cycle to a next ventilation cycle than a possible increase in the volume reserve.

12. An anesthesia apparatus in accordance with claim 10, wherein the change in the zero position of the piston is limited by at least one preset or presettable limit value for a resulting, changed volume reserve.

13. An anesthesia apparatus in accordance with claim 12, wherein:

at least one preset or presettable limit values are taken into account for the setting for the fresh gas feed into the breathing circuit for the selection of the first mode of operation or the second mode of operation and for the switching between the first mode of operation and the second mode of operation; and the limit value is determined automatically based on a demographic variable of the patient.

14. A method for operating an anesthesia apparatus comprising a breathing gas feed unit for displacing a breathing gas volume in a breathing circuit, wherein the breathing gas feed unit comprises a piston bringing about the displacement of the breathing gas, the method comprising the steps of:

automatically switching over between at least one first mode of operation and a second mode of operation during a return of the piston to preset a corresponding piston return velocity; and providing the piston return velocity to depend on a volume flow in an exhalation branch of the breathing circuit in the first mode of operation; and providing the piston return velocity to depend on a minimally necessary piston return velocity in the second mode of operation;

wherein a zero position of the piston of the breathing gas feed unit is changed incrementally as a function of a volume reserve and an applied inspiratory tidal volume;

wherein the zero position of the piston and a changed volume reserve resulting from a change in the zero position of the piston are changed asymmetrically, such that a possible reduction of the volume reserve is smaller from one ventilation cycle to a next ventilation cycle than a possible increase in the volume reserve.

\* \* \* \* \*